(12) United States Patent
Zou et al.

(10) Patent No.: US 11,338,000 B2
(45) Date of Patent: May 24, 2022

(54) **USE OF *BUTYRIBACTER INTESTINI* IN PREVENTING AND/OR TREATING INFLAMMATION-RELATED DISEASES**

(71) Applicant: BGI SHENZHEN, Guangdong (CN)

(72) Inventors: Yuanqiang Zou, Guangdong (CN); Liang Xiao, Guangdong (CN); Xiaoping Li, Guangdong (CN); Jinghong Yu, Guangdong (CN); Chuan Liu, Guangdong (CN)

(73) Assignee: BGI SHENZHEN, Guangdong (CN)

( * ) Notice: Subject to any disclaimer, the term of this patent is extended or adjusted under 35 U.S.C. 154(b) by 2 days.

(21) Appl. No.: 16/769,011

(22) PCT Filed: Dec. 8, 2017

(86) PCT No.: PCT/CN2017/115278
§ 371 (c)(1),
(2) Date: Jun. 2, 2020

(87) PCT Pub. No.: WO2019/109348
PCT Pub. Date: Jun. 13, 2019

(65) Prior Publication Data
US 2021/0085730 A1     Mar. 25, 2021

(51) Int. Cl.
| | | |
|---|---|---|
| *A61K 35/745* | (2015.01) | |
| *A23L 33/135* | (2016.01) | |
| *A61K 39/00* | (2006.01) | |
| *A61K 39/02* | (2006.01) | |
| *A61K 45/00* | (2006.01) | |
| *A61P 29/00* | (2006.01) | |
| *A61K 35/747* | (2015.01) | |

(52) U.S. Cl.
CPC .......... *A61K 35/745* (2013.01); *A23L 33/135* (2016.08); *A61K 35/747* (2013.01); *A61P 29/00* (2018.01)

(58) Field of Classification Search
CPC ............................. A61K 35/745; A23L 33/135
See application file for complete search history.

(56) References Cited

U.S. PATENT DOCUMENTS

| 8,092,793 B2 * | 1/2012 | Cui ................. A61K 35/74 |
| | | 424/93.41 |
| 11,033,614 B2 | 6/2021 | Feng et al. |
| 2013/0288261 A1 * | 10/2013 | Walter .................. A61P 1/14 |
| | | 435/6.12 |
| 2021/0220415 A1 * | 7/2021 | Zou ..................... A61P 1/00 |

FOREIGN PATENT DOCUMENTS

| CN | 105106244 | 12/2015 |
| CN | 105687252 | 6/2016 |
| EP | 3342853 | 7/2018 |
| EP | 3808357 | 4/2021 |
| EP | 3342853 B1 | 10/2021 |
| WO | 2017031985 | 3/2017 |
| WO | 2019227417 | 12/2019 |

OTHER PUBLICATIONS

Lan et al., Scientific Reports, 2016; 6:25587 (Year: 2016).*
Medical News Today, https://www.medicalnewstoday.com/articles/248423#types-and-symptoms; accessed on Sep. 24, 2021 (Year: 2021).*
Barhum, https://www.verywellhealth.com/what-is-inflammation-187934, accessed on Sep. 24, 2021 (Year: 2021).*
https://www.fengchengroup.com/enzymes-and-bio-products/probiotics/clostridium-butyricum-clostridium-butylicum.html (Year: 2021).*
WIPO, ISR for PCT/CN2017/115278, dated Sep. 17, 2018.
Zhang et al., "Therapeutic effects of Clostridium butyricum on experimental colitis induced by oxazolone in rats," World Journal of Gastroenterology, 2009, vol. 15, No. 15, pp. 1821-1828.
EPO, Extended European Search Report for EP Application No. 17934313.2, dated Apr. 21, 2021.
Wang et al., "Inflammation, a Link between Obesity and Cardiovascular Disease," Mediators of Inflammation, 2010, article No. 535918, 17 pages.
Xue et al., "*Butyribacter intestini* gen. nov., sp. nov., a 1 butyric acid-producing bacterium of the family Lachnospiraceae isolated from the human faeces, and reclassification of *Acetivibrio ethanolgignens* as *Acetanaerobacter ethanolgignens* gen. nov., comb, nov.," bioRxiv, 2020, retrieved from the internet: <https://www.biorxiv.org/content/10.1101/2020.09.01.276766v1.full.pdf>, 22 pages.
Fournier et al., "Cautionary tale of using 16S rRNA gene sequence similarity values in identification of human-associated bacterial species," International Journal of Systematic & Evolutionary Microbiology, 2015, vol. 65, No. 6, pp. 1929-1934.
EPO, Communication for EP Application No. 17934313.2, dated Feb. 22, 2022.

* cited by examiner

*Primary Examiner* — Gary B Nickol
*Assistant Examiner* — Lakia J Jackson-Tongue
(74) *Attorney, Agent, or Firm* — Hodgson Russ LLP

(57) ABSTRACT

Provided is a use of *Butyribacter intestini* in preventing and/or treating inflammation-related diseases. Specifically, in the present disclosure, it was firstly discovered that *Butyribacter intestini* has the function of preventing and/or treating inflammation-related diseases (for example, inflammatory bowel disease, such as ulcerative colitis, gastritis, and common enteritis; and rheumatoid arthritis).

18 Claims, 2 Drawing Sheets

USE OF *BUTYRIBACTER INTESTINI* IN PREVENTING AND/OR TREATING INFLAMMATION-RELATED DISEASES

CROSS-REFERENCE TO RELATED APPLICATIONS

This application is a U.S. National Phase application based upon International Application No. PCT/CN2017/115278, filed on Dec. 8, 2017, the entire contents of which is incorporated herein by reference.

FIELD

This present disclosure relates to the field of microorganism, in particular to *Butyribacter intestini* and use thereof in preventing and/or treating inflammation-related diseases.

BACKGROUND

Inflammatory bowel disease (IBD) is a type of chronic inflammatory bowel diseases with unknown etiology, which tends to be recurrent, thus seriously affecting the life quality of patients. Modern medicine believes that the inflammatory bowel disease (IBD) is caused by factors including heredity, diet, infection, autoimmunity, psychological factors, environment and the like. Inflammatory bowel disease includes ulcerative colitis (UC) and Crohn's disease (CD), both of which are inflammation-related diseases.

Ulcerative colitis (UC) is an important type of inflammatory bowel disease (IBD) with unknown etiology, which belongs to a type of chronic bowel diseases and of which the lesion parts are mainly in the submucosa of colonic mucosa. Based on current researches, the main causes of ulcerative colitis are host genetic susceptibility, intestinal flora and intestinal mucosal immune response. The clinical and pathological manifestations of ulcerative colitis are constant abdominal pain, diarrhea, mucous and bloody stools as well as recurrent attacks. The number of UC patients in our country has showed significant upward trend recently.

Currently, the clinical medicines for ulcerative colitis (UC) mainly include salicylic acids, adrenal glucocorticoids and immune agents. Salicylic acid drugs are capable of effectively inhibiting prostaglandin synthesis and scavenging oxygen free radicals, so as to achieve the purpose of alleviating inflammatory response, however, they can only alleviate inflammation in a short time period and cannot cure the UC disease. For the clinical treatment of ulcerative colitis (UC), the commonly used western medicine of salicylic acids is sulfasalazine (SASP), mainly directing to mild, moderate and chronic UC patients. Adrenal glucocorticoids are preferred for severe or paroxysmal UC patients, such as betamethasone. Immune agents, such as cyclosporine, can affect the progress of immune response by inhibiting the generation of T cell IL-2, thereby inhibiting ulcerative colitis (UC).

The three types of existing drugs for ulcerative colitis (UC) can all alleviate UC to some extent, but they also cause certain side effects. Salicylic acids have side effects of generating gastrointestinal reactions, headache, increased reticulocytes, sperm reduction, rash caused by allergic reaction, liver toxicity, leukopenia, anemia and the like, as well as easily caused bacterial flora disorders and enhanced drug resistance due to antibacterial effects of such drugs. Adrenal glucocorticoids can cause side effects such as metabolic disorders, retention of water and the like, which can only be used as emergency medicines and cannot be administered for a long period. Immune agent therapy is highly drug-dependent and has a long treatment cycle, which is likely to cause nephrotoxicity and secondary infection, thus can only be used as an adjuvant therapy.

Therefore, there is an urgent need in the art to develop a new, non-toxic and non-side effect medicament for treating and/or preventing inflammation-related diseases.

SUMMARY

The object of the present disclosure is to provide a new, non-toxic and non-side effect medicament for treating and/or preventing inflammation-related diseases.

In a first aspect, the present disclosure in embodiments provides use of *Butyribacter intestini* in the manufacture of a composition or a preparation for preventing and/or treating inflammation-related diseases.

In another preferred embodiment, the *Butyribacter intestini* includes *Butyribacter intestini* TF01-11.

In another preferred embodiment, the composition is selected from the group consisting of a food composition, a health care composition, a pharmaceutical composition, a beverage composition, a feed composition or a combination thereof.

In another preferred embodiment, the composition is an oral preparation.

In another preferred embodiment, the composition is a liquid preparation, a solid preparation or a semi-solid preparation.

In another preferred embodiment, the dosage form of the composition is selected from the group consisting of powder, pulvis, tablet, sugar coating agent, capsule, granule, suspension, solution, syrup, drop and/or sublingual tablet.

In another preferred embodiment, the food composition includes an emulsion product, a solution product, a powder product or a suspension product.

In another preferred embodiment, the food composition includes dairy, milk powder or milk emulsion.

In another preferred embodiment, the liquid preparation is selected from the group consisting of a solution product or a suspension product.

In another preferred embodiment, the inflammation-related diseases are selected from the group consisting of inflammatory bowel disease, rheumatoid arthritis or a combination thereof.

In another preferred embodiment, the inflammation-related diseases are selected from the group consisting of ulcerative colitis, gastritis, general enteritis or a combination thereof.

In another preferred embodiment, the preparation includes a microecological preparation.

In a second aspect, the present disclosure in embodiments provides use of *Butyribacter intestini* in the manufacture of a composition or a preparation for use in one or more selected from the group consisting of:

(i) controlling weight loss in a mammal;

(ii) decreasing disease activity index (DAI) in a mammal; and (iii) relieving intestinal lesions in a mammal.

In another preferred embodiment, the controlling weight loss in a mammal refers to the weight loss of mammals in an experimental group is not more than 10%, preferably not more than 5%, more preferably not more than 2% compared to the mammals in a model group.

In another preferred embodiment, the relieving intestinal lesions in a mammal includes slowing down the shortening of colon length and/or reducing the inflammation of colon.

In another preferred embodiment, the mammal includes human or non-human mammal.

In another preferred embodiment, the non-human mammal includes rodents such as mice and rats, or primates such as monkey.

In a third aspect, the present disclosure in embodiments provides a composition for use in preventing and/or treating inflammation-related diseases, comprising (a) a safe and effective amount of *Butyribacter intestini*; and (b) a food acceptable or pharmaceutically acceptable carrier.

In another preferred embodiment, the *Butyribacter intestini* includes *Butyribacter intestini* TF01-11.

In another preferred embodiment, the composition further contains a growth factor, preferably a milk growth factor.

In another preferred embodiment, the composition is selected from the group consisting of a food composition, a health care composition, a pharmaceutical composition, a beverage composition, a feed composition or a combination thereof.

In another preferred embodiment, the composition is an oral preparation.

In another preferred embodiment, the composition is a liquid preparation, a solid preparation or a semi-solid preparation.

In another preferred embodiment, the dosage form of the composition is selected from the group consisting of powder, pulvis, tablet, sugar coating agent, capsule, granule, suspension, solution, syrup, drop, sublingual tablet or a combination thereof.

In another preferred embodiment, the food composition includes an emulsion product, a solution product, a powder product or a suspension product.

In another preferred embodiment, the food composition includes dairy products, milk powder, or milk emulsion.

In another preferred embodiment, the liquid formulation is selected from the group consisting of a solution product or a suspension product.

In another preferred embodiment, the composition contains $1\times10$-$1\times10^{15}$ cfu/mL or cfu/g of *Butyribacter intestini*, preferably $1\times10^{4}$-$1\times10^{10}$ cfu/mL or cfu/g of *Butyribacter intestini* based on the total volume or total weight of the composition.

In another preferred embodiment, the composition contains 0.0001 wt % to 99 wt %, preferably 0.1 wt % to 90 wt % of *Butyribacter intestini* based on the total weight of the composition.

In another preferred embodiment, the composition is in a unit dosage form, i.e., one tablet, one capsule or one vial, and the composition in each unit dosage form is of a mass of 0.05 g to 5 g, preferably 0.1 g to 1 g.

In another preferred embodiment, the composition further contains probiotics and/or prebiotics.

In another preferred embodiment, the probiotics are selected from the group consisting of Lactic acid bacteria, *Bifidobacteria, Lactobacillus acidophilus* or a combination thereof.

In another preferred embodiment, the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

In another preferred embodiment, the composition further contains a substance capable of maintaining the viability of *Butyribacter intestini*, such as a protective agent.

In another preferred embodiment, the substance capable of maintaining the viability of *Butyribacter intestini* such as a protective agent is selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof.

In another preferred embodiment, the substance capable of maintaining the viability of *Butyribacter intestini* such as a protective agent is of a weight ratio of 0.1% to 2%, preferably 0.5% to 1.5%, more preferably 0.5% to 1.0%, based on the total weight of the composition.

In another preferred embodiment, the substance capable of maintaining the viability of *Butyribacter intestini* such as a protective agent is of an amount of 1 mg to 20 mg, preferably 5 mg to 15 mg, more preferably 5 mg to 10 mg, based on 1 g of the composition.

In a fourth aspect, the present disclosure in embodiments provides a composition for use in preventing and/or treating inflammatory bowel disease, comprising (a) a safe and effective amount of *Butyribacter intestini*; and (b) a food acceptable or pharmaceutically acceptable carrier.

In another preferred embodiment, the inflammatory bowel disease is selected from the group consisting of ulcerative colitis, gastritis, general enteritis or a combination thereof.

In a fifth aspect, the present disclosure in embodiments provides a composition for use in preventing and/or treating rheumatoid arthritis, comprising (a) a safe and effective amount of *Butyribacter intestini*; and (b) a food acceptable or pharmaceutically acceptable carrier.

In a sixth aspect, the present disclosure in embodiments provides a method for preparing the composition of the third aspect to the fifth aspect, comprising a step of:

mixing (i) *Butyribacter intestini* with (ii) a food acceptable or pharmaceutically acceptable carrier to form the composition of the third aspect to the fifth aspect.

In another preferred embodiment, the method further includes a step of mixing with a growth factor.

In another preferred embodiment, the method further includes a step of mixing with a substance capable of maintaining the viability of *Butyribacter intestini*, such as a protective agent.

In another preferred embodiment, the composition further contains a substance (such as a protective agent) that being capable of maintaining the vitality of *Butyribacter intestini*.

In another preferred embodiment, the substance capable of maintaining the viability of *Butyribacter intestini* such as a protective agent is selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof.

In another preferred embodiment, the method further includes a step of mixing with probiotics and/or prebiotics.

In another preferred embodiment, the probiotics are selected from the group consisting of Lactic acid bacteria, *Bifidobacteria, Lactobacillus acidophilus* or a combination thereof.

In another preferred embodiment, the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

In another preferred embodiment, the growth factor is a milk growth factor.

In another preferred embodiment, the growth factor is selected from the group consisting of vitamins, purines, pyrimidines or a combination thereof.

In another preferred embodiment, the composition is an oral preparation.

In a seventh aspect, the present disclosure in embodiments provides a method for relieving intestinal lesions in a mammal, comprising administering the composition of the third aspect to the fifth aspect to a subject.

In another preferred embodiment, the composition is administered orally.

In another preferred embodiment, the administration dosage is 0.01 to 5 g/50 kg body weight per day, preferably 0.1 to 2 g/50 kg body weight per day.

In another preferred embodiment, the subject includes human or non-human mammal.

In another preferred embodiment, the non-human mammal includes rodents such as mice and rats, and primates such as monkey.

In another preferred embodiment, the method is non-therapeutic or non-diagnostic.

In an eighth aspect, the present disclosure in embodiments provides a method for controlling weight loss in a mammal and/or reducing disease activity index (DAI) in a mammal, comprising administering the composition of the third aspect to the fifth aspect to a subject.

In another preferred embodiment, the composition is administered orally.

In another preferred embodiment, the administration dosage is 0.01 to 5 g/50 kg body weight per day, preferably 0.1 to 2 g/50 kg body weight per day.

In another preferred embodiment, the subject includes human or non-human mammal.

In another preferred embodiment, the non-human mammal includes rodents such as mice and rats, and primates such as monkey.

In another preferred embodiment, the method is non-therapeutic or non-diagnostic.

In a ninth aspect, the present disclosure in embodiments provides a method for preventing and/or treating inflammation-related diseases, comprising a step of administering the composition of the third aspect to the fifth aspect to a subject, thereby preventing and/or treating inflammation-related diseases.

In another preferred embodiment, the composition is administered orally.

In another preferred embodiment, the administration dosage is 0.01 to 5 g/50 kg body weight per day, preferably 0.1 to 2 g/50 kg body weight per day.

In another preferred embodiment, the subject includes human or non-human mammal.

In another preferred embodiment, the non-human mammal includes rodents such as mice and rats, and primates such as monkey.

In another preferred embodiment, the method is non-therapeutic or non-diagnostic.

It should be understood that, the technical features of the present disclosure as described above and the technical features as specifically described below (such as examples) may be combined with each other to form a new or preferred technical solution within the scope of the present disclosure, which will not be repeated due to limited space.

DETAILED DESCRIPTION

Figure 1:
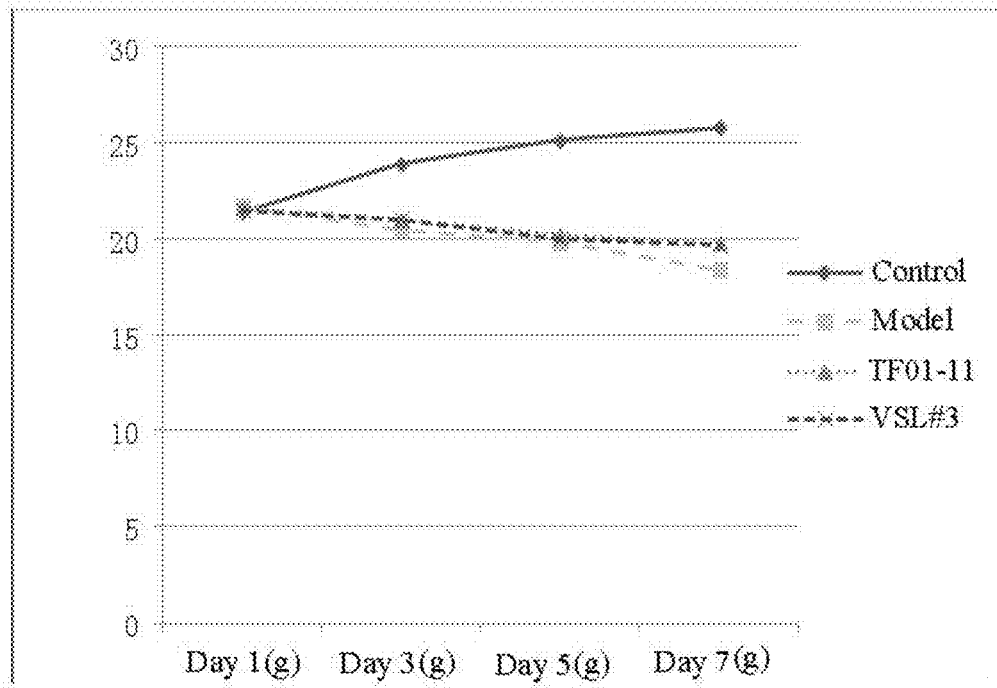
FIG. 1 shows the weight changes of mice in the control group, model group, and VSL$^\#$3 and TF01-11 treatment groups. It can be seen from FIG. 1 that the weight of mice in the control group is slowly increased, while the weight of mice in the DSS-induced model group continues to decrease. On day 7, the weight loss of mice in the model group is most significant compared to the control group, while the treatment of *Butyribacter intestini* TF01-11 and VSL$^\#$3 can slow down the weight loss of UC mice. On day 7, the weight loss of mice in the TF01-11 and VSL$^\#$3 groups was controlled significantly compared to the model group, showing the two probiotic bacteria can control the weight loss caused by UC disease. The weight of mice in the TF01-11 group on day 7 is slightly higher than the VSL$^\#$3 group, indicating that the *Butyribacter intestini* TF01-11 exhibits a slightly better efficacy than VSL$^\#$3 on controlling weight loss of UC mice.

Present inventors have surprisingly discovered that strain *Butyribacter intestini* exhibits the efficacy of preventing and/or treating inflammation-related diseases (for example, inflammatory bowel disease (such as ulcerative colitis, gastritis and general enteritis) and rheumatoid arthritis) after extensive and intensive researches and experiments. It is found that the active composition containing the *Butyribacter intestini* of the present disclosure is capable of controlling weight loss, decreasing disease activity index (DAI) and relieving intestinal lesions, thus can effectively alleviate symptoms of inflammation-related diseases (for example, inflammatory bowel disease (such as ulcerative colitis, gastritis and general enteritis) and rheumatoid arthritis) and the like through feeding the active composition to experimental subjects. On this basis, the present inventors have accomplished the present disclosure.

As used herein, the term "comprising" means that various components can be applied together in a mixture or a composition of the present disclosure. Accordingly, the terms "essentially consisting of . . . " and "consisting of . . . " are included in the scope of the term "comprising".

As used herein, the term "growth factor" includes a milk growth factor, specifically including nutrients of vitamins, purines, pyrimidines or a combination thereof.

In which, the vitamins include but are not limited to Vitamin C, Vitamin E, Vitamin A, Vitamin A precursor, Vitamin $B_6$, Vitamin $D_3$, Vitamin K, folic acid or a combination thereof;

the purines include but are not limited to purine nucleosides, which include 5'-phosphate esters of purine nucleosides;

the 5'-phosphate esters of purine nucleosides are selected from the group consisting of inosinic acid (inosine-5'-phosphate ester; IMP), guanylic acid (guanosine-5'-phosphate ester; GMP), xanthylic acid (xanthosine-5'-phosphate ester; XMP), adenylic acid (adenosine-5'-phosphate ester; AMP) or a combination thereof the pyrimidines include all substances containing a pyrimidine structure.

As used herein, the terms "controlling weight loss in a mammal", "slowing down weight loss in a mammal", "controlling weight decrease in a mammal" and "slowing down weight decrease in a mammal" can be used interchangeably and refer to the body weight of experimental animals is decreased during the establishment of ulcerative colitis model due to the increasing severity of inflammation. The weight loss percentage is the percentage of decreased body weight to initial body weight. The higher the body weight decreases, the more serious the disease is. During the treatment of ulcerative colitis in a mammal, the *Butyribacter intestini* of the present disclosure can control the weight loss of experimental animals and alleviate the symptoms of disease.

Disease Activity Index (DAI)

As used herein, the term "disease activity index" refers to a comprehensive score of three indicators (i.e., the weight loss percentage, stool viscosity and stool bleeding) in a patient or an affected animal.

*Butyribacter intestini* and Application Thereof

As used herein, the term "strain *Butyribacter intestini*", "*Butyribacter intestini*" and "*Butyribacter intestini* of the present disclosure" can be used interchangeably. Physiological characteristics of the *Butyribacter intestini* of the present disclosure are shown as follows. The colony of *Butyribacter intestini* shows an off-white, opaque and smooth appearance with a pseudo-root like irregular edge, and has a diameter of about 2 mm after culturing in a plate containing peptone yeast extract glucose (PYG) medium under an anaerobic condition at 37° C. for 48 hours. The *Butyribacter intestini* TF01-11 is identified to be Gram-positive bacterium through Gram staining and microscope observation. The *Butyribacter intestini* TF01-11 is rod-like, does not generate spores, and have flagella and is moveable. The bacterium is about 0.5 to 1.0 mm in diameter and about 2.0 to 8.0 mm in length. The *Butyribacter intestini* of the present disclosure is negative to catalase, which proliferates in a temperature range of 30 to 42° C. preferably at 37° C., and is tolerant to a pH range of 6.0-8.5 and 2% NaCl. *Butyribacter intestini* can produce several carbohydrates after fermentation, including xylose, galactose, raffinose, glucose, maltose, cellobiose, sucrose, starch and glycogen, and produce mainly acetic acid and butyric acid.

In a preferred embodiment, the *Butyribacter intestini* includes *Butyribacter intestini* TF01-11.

The present disclosure provides use of *Butyribacter intestini* in preventing and/or treating inflammation-related diseases, for example, inflammatory bowel disease (such as ulcerative colitis, gastritis, general enteritis), and rheumatoid arthritis. Dextran sodium sulfate (DSS) is used to induce a model in a subject. The strain *Butyribacter intestini* TF01-11 is for use in one or more selected from the group consisting of (i) controlling weight loss in a subject, (ii) decreasing disease activity index (DAI), and (iii) relieving intestinal lesions. According to a preferred embodiment of the present disclosure, C57bl/6 mice are used as experimental mice and dextran sodium sulfate (DSS) is used to induce a model, thus obtaining the ulcerative colitis (UC) mouse model, which is then treated with *Butyribacter intestini* TF01-11. The *Butyribacter intestini* TF01-11-treated UC mouse model exhibits slowing down of weight loss, and alleviated indicators associated with inflammation-related diseases (for example, inflammatory bowel disease (such as ulcerative colitis, gastritis, general enteritis), and rheumatoid arthritis), such as relieving intestinal lesions (including slowing down the shortening of colon length, reducing the inflammation reaction in colon and the like), decreasing disease activity index (DAI) and the like, compared to the untreated control group (i.e. a model group). Therefore, the strain can be useful in preventing and/or treating inflammation-related diseases, such as inflammatory bowel diseases (such as ulcerative colitis, gastritis, general enteritis), and rheumatoid arthritis.

Composition and Application Thereof

The present disclosure also provides a composition. Preferably, the composition includes a food composition, a health care composition, a pharmaceutical composition, a beverage composition or a feed composition. More preferably, the composition is a pharmaceutical composition. The composition contains an effective amount of *Butyribacter intestini*. In a preferred embodiment, the composition further contains a growth factor, such as a milk growth factor. In a preferred embodiment, the composition further contains probiotics selected from the group consisting of Lactic acid bacteria, *Bifidobacteria, Lactobacillus acidophilus* or a combination thereof and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Butyribacter intestini* (such as a protective agent), which includes cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof. The substance capable of maintaining the viability of *Butyribacter intestini* (such as a protective agent) is of a weight ratio of 0.1% to 2%, preferably 0.5% to 1.5%, more preferably 0.5% to 1.0%, based on the total weight of the composition.

In a preferred embodiment, the composition is a liquid preparation, a solid preparation or a semi-solid preparation.

In a preferred embodiment, the liquid preparation is selected from the group consisting of a solution product or a suspension product.

In a preferred embodiment, the dosage form of the composition is selected from the group consisting of powder, pulvis, tablet, sugar coating agent, capsule, granule, suspension, solution, syrup, drop, sublingual tablet or a combination thereof.

The composition of the present disclosure may be administered in any form of oral solution, tablet, injection, orally disintegrating tablet, lyophilized powder or capsule, preferably in the dosage form of enteric agent (such as capsule). In the present disclosure, the used excipient, pharmaceutically acceptable vehicle and carrier are mainly selected depending on the property suitable for the bacteria or metabolites thereof and the specific administration means required, which is beneficial to the smooth passage of the bacteria or metabolites thereof through stomach thus absorbed by the administered subject, without special indication. These substances can be selected according to the administration route.

The composition of the present disclosure may further contain any additional excipients among those commonly useful in pharmaceutical preparations, for example, for stabilization of the composition itself, or allowing to be easily dispersed or imparting a suitable taste.

Among the excipients, suitable examples are inulin, fructose, starch, xylooligosaccharide, silicon dioxide, buffering agent and flavoring agent.

The pharmaceutical preparation of the present disclosure may further contain an auxiliary active component.

Lactose, maltodextrin, glucose, sucrose, sorbitol, mannose, starch, arabic gum, calcium phosphate, alginate, gelatin, calcium silicate, fine crystalline cellulose, polyvinylpyrrolidone (PVP), cellulose, water, syrup, methyl cellulose, methyl hydroxybenzoate, propyl hydroxybenzoate, talc, magnesium stearate, mineral oil and the like can be all used as carriers, excipients, diluents and the like of the pharmaceutical composition of the present disclosure.

Further, the pharmaceutical composition of the present disclosure may further contain lubricant, wetting agent, emulsifier, suspension stabilizer, preservative, sweetening agent, flavor and the like. The pharmaceutical composition of the present disclosure can be produced in an enteric coating preparation via a variety of well-known methods, so that the active component of the pharmaceutical composition (i.e., the microorganism) can pass through stomach smoothly without destroyed by gastric acid.

Further, the microorganism of the present disclosure may be used in the form of capsule prepared by conventional methods. For example, standard excipients and lyophilized microorganism of the present disclosure are mixed to obtain pills which are subsequently dispensed into gelatin capsules. In addition, the microorganism of the present disclosure and pharmaceutically acceptable excipients (such as liquid gum, cellulose, silicate, mineral oil and the like) can be mixed and prepared in suspension or dispersion, and such a suspension or dispersion can be filled into soft gelatin capsules.

The pharmaceutical composition of the present disclosure can be prepared in enteric coating tablets for oral use. The term "enteric coating" in the present disclosure includes all coatings that are allowed for conventional drugs. These coatings are not degraded by gastric acid, however, can be completely broken down in small intestine and then quickly release the microorganism of the present disclosure. The enteric coating of the present disclosure can be maintained in a HCl solution for gastric acid synthesis (such as pH=1) at 36° C. to 38° C. for more than 2 hours, preferably broken down in a buffer solution for intestinal fluid synthesis (such as pH=7.0) within one hour.

The enteric coating of the present disclosure is coated in an amount of about 16 to 30 mg per tablet, preferably 16 to 25 mg per tablet, and more preferably 16 to 20 mg per tablet. The thickness of the enteric coating in the present disclosure is 5 to 100 μm, ideally 20 to 80 μm. The components of enteric coating are selected from conventional polymers which are known in public.

The preferred enteric coating of the present disclosure is prepared by a copolymer of cellulose acetate phthalate polymer or cellulose acetate trimellitate polymer and methacrylic acid, for example, a copolymer of methacrylic acid and methylcellulose hydroxypropyl phthalate or its ester derivatives, in which the amount of methacrylic acid is more than 40%.

The cellulose acetate phthalate used in the enteric coating of the present disclosure has a viscosity of about 45 to 90 cp, an acetyl content of 17 to 26%, and a phthalic acid content of 30 to 40%. The cellulose acetate trimellitate used in the enteric coating has a viscosity of about 5 to 21 cp, and an acetyl content of 17 to 26%. Cellulose acetate trimellitate, produced by Eastman Kodak Company, can be used as the enteric coating material in the present disclosure.

The hydroxypropyl methylcellulose phthalate used in the enteric coating of the present disclosure generally has a molecular weight of 20,000 to 130,000 Daltons (ideally 80,000 to 100,000 Daltons), a hydroxypropyl content of 5 to 10%, a methoxyl content of 18 to 24% and a phthaloyl content of 21 to 35%.

The hydroxypropyl methylcellulose phthalate used in the enteric coating of the present disclosure is HP50, produced by Shin-Etsu Chemical Co. Ltd. of Japan. HP50 contains 6 to 10% of hydroxypropyl, 20 to 24% of methoxy and 21 to 27% of propyl, with a molecular weight of 84,000 Daltons. Another enteric coating material is HP55, which contains 5 to 9% of hydroxypropyl, 18 to 22% of methoxy and 27 to 35% of phthalic acid, with a molecular weight of 78,000 Daltons.

The enteric coating of the present disclosure is prepared by spraying the enteric coating solution onto the core through conventional methods. Solvents for the enteric coating method are alcohols (such as ethanol), ketones (such as acetone), halogenated hydrocarbon compounds (such as dichloromethane) or a combination thereof. Softeners such as di-n-butyl phthalate and glyceryl triacetate are added to the enteric coating solution in a ratio of 1 part of the coating to about 0.05 parts (or about 0.3 parts) of the softener. The spraying method is preferably performed continuously, and the amount of spray material can be controlled according to the conditions for coating. The spraying pressure can be adjusted flexibly, generally, an average pressure of 1 to 1.5 Pa will result in ideal results.

The "pharmaceutically effective amount" in the specification refers to an amount which is functional or active to human and/or animals and is acceptable to human and/or animals. For example, a preparation containing $1 \times 10$-$1 \times 10^{15}$ cfu/ml or cfu/g (particularly $1 \times 10^4$-$1 \times 10^{10}$ cfu/ml or cfu/g, more particularly $1 \times 10^6$-$1 \times 10^{10}$ cfu/ml or cfu/g) of *Butyribacter intestini* and/or metabolites thereof can be prepared in the present disclosure.

When the *Butyribacter intestini* is used in the manufacture of a pharmaceutical composition, the effective dosage of *Butyribacter intestini* or metabolites thereof used may vary depending on the administration route and the severity of disease to be treated. A dosage form suitable for internal administration includes about $1 \times 10$-$1 \times 10^{15}$ cfu/ml or cfu/g (particularly $1 \times 10^4$-$1 \times 10^{10}$ cfu/ml or cfu/g, more particularly $1 \times 10^6$-$1 \times 10^{10}$ cfu/ml or cfu/g) of active *Butyribacter*

*intestini* or its active component produced by fermentation, which is closely mixed with a solid or liquid pharmaceutically acceptable carrier. This dosage regimen can be adjusted to provide the best therapeutic response. For example, several divided doses may be administered daily, or the dosage may be proportionally reduced according to the urgent need of treatment condition.

The *Butyribacter intestini* or metabolites thereof may be administered by oral route and the like. Solid carriers include starch, lactose, dicalcium phosphate, microcrystalline cellulose, sucrose and white clay; and liquid carriers include culture medium, polyethylene glycol, non-ionic surfactants and edible oils (such as corn oil, peanut oil and sesame oil), as long as they are suitable for the property of *Butyribacter intestini* or metabolites thereof and the specific administration means required. Adjuvants commonly used in the manufacture of pharmaceutical composition may also be advantageously included, for example, flavoring agents, pigments, preservatives and antioxidants such as Vitamin E, Vitamin C, BHT and BHA.

From the standpoint of ease of manufacture and administration, preferred pharmaceutical composition is the solid composition, especially tablets and/or solid-filled or liquid-filled capsules. Preferred is oral administration.

The composition of the present disclosure is administered to individuals once or several times per day. The dosage unit of administration refers to a dosage that is physically separated and suitable for application in human or all individuals of other mammals. Each unit contains a pharmaceutically acceptable carrier and a therapeutically effective amount of microorganism of the present disclosure. The administration dosage varies with the body weight and severity of inflammation-related diseases (for example, inflammatory bowel disease (such as ulcerative colitis, gastritis, general enteritis), rheumatoid arthritis) in a patient, the contained supplementary active components and the microorganism used. Further, if possible, the composition can be administered separately and continuously as necessary. Therefore, the administration dosage does not limit the scope of the present disclosure. In addition, the "composition" in the present disclosure means not only a medicament but also a functional food and a health supplement food. In a preferred embodiment, the composition includes beverage, food, medicine, animal feed and the like.

In a preferred embodiment, the present disclosure further provides a food composition, which contains an effective amount of *Butyribacter intestini* and/or metabolites thereof as well as a food acceptable carrier as balance. The dosage form of the food composition is selected from a solid product, a dairy product, a solution product, a powder product or a suspension product. In a preferred embodiment, the food composition may further contain a growth factor, such as a milk growth factor. In a preferred embodiment, the composition further contains probiotics selected from the group consisting of Lactic acid bacteria, *Bifidobacteria*, *Lactobacillus acidophilus* or a combination thereof and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Butyribacter intestini* (such as a protective agent), including cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof.

In a preferred embodiment, the composition has the following formula:
  $1 \times 10 - 1 \times 10^{15}$ cfu/mL of *Butyribacter intestini* and/or metabolites thereof and
  a food or pharmaceutically acceptable carrier and/or excipient.

In another preferred embodiment, the composition has the following formula:
  $1 \times 10^{4} - 1 \times 10^{10}$ cfu/mL of *Butyribacter intestini* and/or metabolites thereof and
  a food or pharmaceutically acceptable carrier and/or excipient.

Microecological Preparation

Microecological preparation is a biological preparation containing probiotics and metabolites thereof or a dietary supplement agent that can supply probiotics, which are capable of adjusting and maintaining the microecological balance in intestine, thus achieving the purpose of improving human health. The microecological preparation mainly includes probiotics, prebiotics and synbiotics.

In the present disclosure, the microecological preparation contains (a) a safe and effective amount of *Butyribacter intestini* and/or metabolites thereof and (b) a food acceptable or pharmaceutically acceptable carrier. In a preferred embodiment, the preparation further contains a growth factor, such as a milk growth factor, preferably including vitamins, purines and/or pyrimidines. In a preferred embodiment, the preparation further contains probiotics selected from the group consisting of Lactic acid bacteria, *Bifidobacteria*, *Lactobacillus acidophilus* or a combination thereof and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Butyribacter intestini* (such as a protective agent) selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof.

Culture Method of *Butyribacter intestini*

In the present disclosure, the *Butyribacter intestini* is cultured in peptone yeast extract glucose (PYG) medium (purchased from Huankai Microbiology Technology Co., Ltd.) at 37° C. for 48 to 78 hours.

Method for Relieving Intestinal Lesions in a Mammal

In another preferred embodiment, the method includes ingesting a pharmaceutical composition, a food composition, a beverage composition or a combination thereof of the present disclosure. The experimental subject is a mammal, such as human.

In another preferred embodiment, the method includes ingesting a pharmaceutical composition, a food composition, an animal feed or a combination thereof of the present disclosure. The experimental subject is animals, preferably mice or rabbit.

Method for Controlling Weight Loss and/or Decreasing Disease Activity Index (DAI) in a Mammal In another preferred embodiment, the method includes ingesting a pharmaceutical composition, a food composition, a beverage composition or a combination thereof of the present disclosure. The experimental subject is a mammal, such as human.

In another preferred embodiment, the method includes ingesting a pharmaceutical composition, a food composition, an animal feed or a combination thereof of the present disclosure. The experimental subject is animals, preferably mice or rabbit.

Method for Preventing and/or Treating Inflammation-Related Diseases

In another preferred embodiment, the method includes ingesting a pharmaceutical composition, a food composition, a beverage composition or a combination thereof of the present disclosure. The experimental subject is a mammal, such as human.

In another preferred embodiment, the method includes ingesting a pharmaceutical composition, a food composition, an animal feed or a combination thereof of the present disclosure. The experimental subject is animals, preferably mice or rabbit.

The advantages of the present disclosure mainly include the followings:

(a) *Butyribacter intestini* of the present disclosure is capable of significantly alleviating indicators associated with inflammation-related diseases (for example, inflammatory bowel disease (such as ulcerative colitis, gastritis, general enteritis), rheumatoid arthritis), for example, controlling weight loss, relieving intestinal lesions (including slowing down of the shortening of colon length, reducing the inflammation reaction in colon and the like), decreasing disease activity index (DAI) and the like.

(b) *Butyribacter intestini* of the present disclosure exhibits the following treatment efficacy on UC mice: effectively controlling weight loss of UC mice induced by DSS, inhibiting the increase of disease activity index (DAI) of mice, and relieving intestinal lesions of mice.

(c) *Butyribacter intestini* of the present disclosure has a significant alleviating effect on ulcerative colitis, specifically manifested in capable of significantly ameliorating the pathological phenotype of mice with ulcerative colitis, specifically controlling weight loss of mice, reducing disease activity index (DAI) of mice and controlling the shortening of colon length in UC mice.

The present disclosure is further described below with reference to specific embodiments. It should be understood that these examples are only for illustrating the present disclosure and not intended to limit the scope of the present disclosure. The conditions of experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions.

Unless otherwise specified, the materials and agents used in the examples are all commercially available products.

Example 1 Treatment of *Butyribacter intestini* TF01-11 on UC Mice

The mouse model selected in this example was an ulcerative colitis mouse model induced by dextran sodium sulfate (DSS, the molecular weight of 36000 to 50000, purchased from MPBIO of USA), which was established by continually feeding 0.15% of DSS to C57bl/6 mice for 7 days. The C57bl/6 mice used were purchased from Hubei Medical Laboratory Animal Center. They were 8 months, 20 g±2 g in weight and housed in the animal facility of Specific Pathogen Free (SPF) level.

A total of 48 experimental mice were randomly divided into 4 groups, i.e., 12 mice per group, including:

a normal group (i.e. a control group), in which each mouse was fed with the common feed;

a model group (induced by DSS), in which each mouse was intragastrically given with 0.2 ml of phosphate buffer solution (PBS) per day;

TF01-11 treatment group (induced by DSS), in which each mouse was intragastrically given with 0.2 ml of *Butyribacter intestini* TF01-11 (sourced from BGI SHENZHEN, under a deposit number of CGMCC 10984) bacterial solution per day;

VSL#3 treatment group (induced by DSS), in which each mouse was intragastrically given with 0.2 ml of probiotics VSL#3 (purchased from Alfasigma of USA, therapeutic probiotics for UC in clinic) per day.

The *Butyribacter intestini* TF01-11 treatment process included culturing the *Butyribacter intestini* TF01-11 bacterial solution for 24 hours, collection of bacterial cells via centrifugation, suspension with phosphate buffer solution (PBS), adjustment of bacteria concentration to $10^9$ cfu/ml, and intragastrical administration of 200 μl/day to each mouse.

The VSL#3 treatment process also included suspension with phosphate buffer solution (PBS), adjustment of probiotics concentration to $10^9$ cfu/ml, and intragastrical administration of 200 μl VSL#3/day to each mouse.

*Butyribacter intestini* TF01-11 and VSL#3 were respectively administered intragastrically to mice at the first 3 days before DSS modeling. DSS was added to the drinking water for mice, and the UC model was established by allowing mice receive the drinking water containing DSS ad libitum for 7 days. The body weight, diet and water consumption of mice were recorded daily, and the fecal characteristics and fecal occult blood of mice were also observed. The disease activity index (DAI) of mice on day 1, day 3, day 5 and day 7 was calculated according to the DAI scoring standard on Table 1. Mice were sacrificed after completion of experiment, and all mice were subjected to blood sampling, sacrificed by cervical dislocation, collection of colon tissue, photographed, weighed and measurement of colon length. Colon tissue was stored in a refrigerator at −80° C. and in paraformaldehyde.

TABLE 1

DAI Index Scoring Table

| Weight loss (%) | fecal characteristics | fecal occult blood | Score |
|---|---|---|---|
| 0 | normal feces | normal feces | 0 |
| 1-5 | | | 1 |
| 5-10 | loose stool | presence of blood | 2 |
| 10-15 | | | 3 |
| >15 | watery diarrhea | visible bleeding | 4 |

The fecal characteristics in table is specifically described as that the normal feces means the feces is shaped; the loose stool means the feces is viscous and semi-shaped but not adheres to anus; and the watery diarrhea means the feces is watery and can adhere to anus. The fecal occult blood in table is specifically described as that the normal feces means occult blood is negative; the visible bleeding means the feces has red or brown blood; and the presence of blood means the blood is not naked-eye visible but can be detected with tetramethyl benzidine. The DAI index refers to the sum of integral of weight loss, fecal characteristics and fecal occult blood.

In the following, the therapeutic effect on DSS-induced UC mouse model was measured by comparison of weight loss, DAI and colon length respectively.

1.1 Weight Changes

The weight changes of mice before and after treatment are shown in Table 2 and FIG. 1 as below:

TABLE 2

| Groups | Day 1 (g) | Day 3 (g) | Day 5 (g) | Day 7 (g) |
|---|---|---|---|---|
| Control group | 21.41 ± 0.38 | 23.93 ± 0.58 | 25.13 ± 1.01 | 25.81 ± 1.32 |
| Model group | 21.72 ± 0.47 | 20.51 ± 0.74* | 19.84 ± 1.12* | 18.41 ± 1.37*** |
| TF01-11 group | 21.64 ± 0.51 | 20.98 ± 0.65 | 20.21 ± 0.97 | 19.81 ± 1.32▲ |
| VSL#3 group | 21.50 ± 0.61 | 21.02 ± 0.74 | 20.14 ± 1.28 | 19.68 ± 1.59▲ |

The results in Table 2 show that the weight of mice in the control group is slowly increased, while the weight of mice in the three DSS-induced groups continues to decrease. On day 3, the weight of mice in the model group began to decrease significantly compared to the control group (*P<0.05). On day 7, the weight difference between the model group and the control group was more significant (**P<0.01). The intervention of *Butyribacter intestini* TF01-11 and VSL#3 can slow down the weight loss of UC mice. On day 7, the weight loss of mice in the TF01-11 and VSL#3 groups was controlled significantly compared to the model group (▲P<0.05). The results show that the *Butyribacter intestini* TF01-11 and VSL#3 can control the weight loss caused by UC disease. On day 7, the weight of mice in the TF01-11 group was slightly higher than the VSL#3 group, indicating that the *Butyribacter intestini* TF01-11 is capable of achieving a same effect as or even a better effect over VSL#3 on controlling weight loss of UC mice.

1.2 DAI Changes

DAI index of DSS-induced UC mice was changed due to the changes in weight loss, fecal characteristics and fecal occult blood. Changes in DAI index of mice before and after treatment are shown in Table 3 and FIG. 2.

TABLE 3

| Groups | Day 1 (g) | Day 3 (g) | Day 5 (g) | Day 7 (g) |
|---|---|---|---|---|
| Control group | 1.1 ± 0.2 | 1.1 ± 0.4 | 1.2 ± 0.7 | 1.2 ± 0.9 |
| Model group | 1.1 ± 0.3 | 3.5 ± 1.2* | 6.6 ± 1.5** | 8.9 ± 2.0** |
| TF01-11 group | 1.2 ± 0.4 | 3.3 ± 0.8 | 5.4 ± 1.2▲ | 7.2 ± 1.6▲ |
| VSL#3 group | 1.1 ± 0.4 | 3.1 ± 1.0 | 5.7 ± 1.4 | 7.6 ± 1.7▲ |

Figure 2:
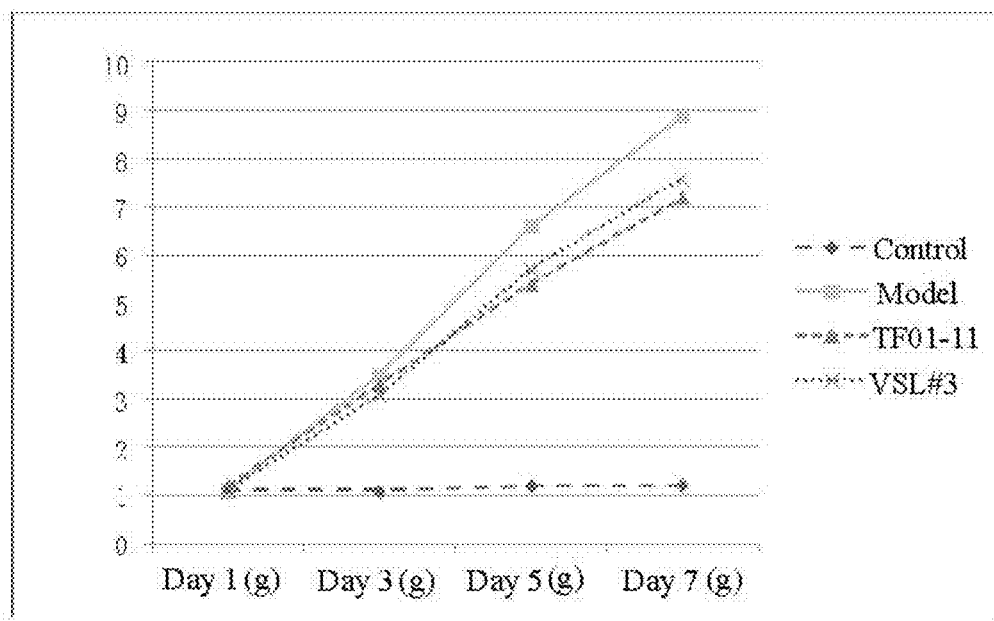
FIG. 2 shows the DAI changes of mice in the control group, model group, and VSL$^\#$3 and TF01-11 treatment groups. It can be seen from FIG. 2 that the DAI of mice in the control group retains a positive constant and low level, while the DSS-induced mice develop increasing DAI level due to a series of pathologies. DAI of mice in the model group becomes significant over the control group on day 3, and reaches the highest level on day 7. The intervention of probiotic bacteria can control the DAI increase, specifically, DAI of mice in the TF01-11 group reaches a significant level relative to the model group on day 5, and DAI of mice in the TF01-11 and VSL$^\#$3 groups is controlled to an extent relative to the model group on day 7. The DAI of mice in the TF01-11 group on day 7 is slightly lower than the VSL$^\#$3 group, indicating that the *Butyribacter intestini* TF01-11 exhibits a slightly better efficacy than VSL$^\#$3 on controlling DAI increase of UC mice.

The data in Table 3 and FIG. 2 show that the DAI of mice in the control group is basically unchanged, while the DAI of mice in the model group, the TF01-11 and VSL#3 groups is gradually increased with the induction of DSS. On day 3, the DAI of mice in the model group began to increase significantly compared to the control group (*P<0.05). On day 7, the DAI of mice in the model group reached the highest level compared to the control group (**P<0.01). The intervention of probiotic bacteria can control the increase of DAI, in which the DAI of mice in the TF01-11 group is significantly controlled on day 5 compared to the model group (▲P<0.05); the DAI of mice in the TF01-11 and VSL#3 groups is significantly lower than the model group on day 7 (▲P<0.05). The DAI of mice in the TF01-11 group is slightly lower than the VSL#3 group, which indicates that the *Butyribacter intestini* TF01-11 is capable of achieving a same effect as or even a better effect over VSL#3 on controlling DAI increase of UC mice.

1.3 Changes of Colon Length

The colon tissue of UC model mice can be changed because the ulcers and inflammation cause the shortening of colon tissue. After the treatment, the colon length of mice measured by anatomy is shown in Table 4 and FIG. 3.

TABLE 4

| Groups | Colon length |
|---|---|
| Control group | 8.01 ± 0.69 |
| Model group | 5.53 ± 0.64** |
| VSL#3 group | 6.21 ± 0.73▲ |
| TF01-11 group | 6.23 ± 0.85▲ |

Figure 3:
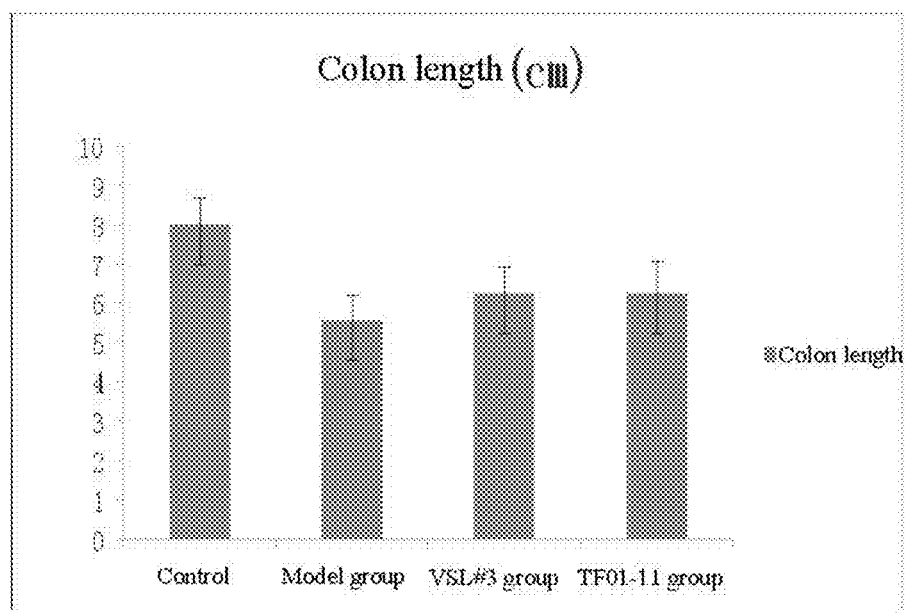
FIG. 3 shows the colon length of mice in the control group, model group, and VSL #3 and TF01-11 treatment groups. It can be seen from FIG. 3 that the colon length of mice in the model group is significantly shorter than the control group on day 7 due to a series of pathologies induced by DSS. The intervention of probiotic bacteria can control the shortening of colon length. The colon length of mice in the TF01-11 and VSL$^\#$3 groups reaches a significant level relative to the model group on day 7. According to the colon length on day 7, it can be seen that the *Butyribacter intestini* TF01-11 exhibits a same efficacy as VSL$^\#$3 on controlling the shortening of colon length of UC mice.

The results in Table 4 and FIG. 3 show that the colon tissue of mice in the model group is shortened significantly 7 days after DSS induction, which is also greatly significant compared to the control group (**P<0.01). The intervention of probiotic bacteria (i.e. *Butyribacter intestini* TF01-11 and VSL#3) can significantly control the colon shortening of mice, which is very significant compared to the model group (*P<0.05). According to the data in Table 4, it can be seen that the *Butyribacter intestini* TF01-11 is capable of achieving a same effect as VSL#3 on controlling the colon length shortening of UC mice.

Example 2 Food Composition Containing *Butyribacter intestini* TF01-11

Raw materials and proportion thereof were shown in Table 5.

TABLE 5

| Raw materials | Mass percentage (%) |
|---|---|
| *Butyribacter intestini* TF01-11 | 0.5 |
| milk | 90.0 |
| sugar | 9.0 |
| Vitamin C | 0.5 |

Milk and sugar in proportion according to formula as above were mixed, stirred to completely mix, preheated, homogenized at the pressure of 20 Mpa, and then sterilized at about 90° C. for 5 to 10 mins, cooled to 40 to 43° C., followed by adding a protective agent (Vitamin C) and inoculation of 1-100×10$^6$ cfu/g *Butyribacter intestini* TF01-11, thus obtaining the food composition containing *Butyribacter intestini* TF01-11.

Example 3 Pharmaceutical Composition Containing *Butyribacter intestini* TF01-11

Raw materials and proportion thereof were shown in Table 6.

TABLE 6

| Raw materials | Mass percentage (%) |
|---|---|
| *Butyribacter intestini* TF01-11 | 1.0% |
| lactose | 2.0% |
| yeast powder | 2.0% |
| peptone | 1.0% |
| purified water | 93.5% |
| Vitamin C | 0.5% |

Lactose, yeast powder and peptone in the proportion were mixed with purified water to be uniform, preheated to 60 to 65° C., homogenized at the pressure of 20 Mpa, and then sterilized at about 90° C. for 20 to 30 mins, cooled to 36 to 38° C., followed by adding vitamin C and inoculation of 1-50×10$^6$ cfu/mL active *Butyribacter intestini* TF01-11, after which fermented at 36 to 38° C. to pH 6.0, centrifuged, freeze-dried to less than 3% of water content, thus obtaining a freeze-dried product containing *Butyribacter intestini* TF01-11. 0.5 g of the freeze-dried product containing *Butyribacter intestini* TF01-11 was weighed, mixed with an equal amount of maltodextrin and a protective agent (such as vitamin C, cysteine), and then encapsulated into capsules, thus obtaining the pharmaceutical composition containing *Butyribacter intestini* TF01-11.

Example 4 Manufacture of a Medicament for Treating Inflammation-Related Diseases Such as Ulcerative Colitis (UC)

4.1 Preparation of Bacterial Solution

*Butyribacter intestini* TF01-11 (1×10$^9$ cfu/ml) was anaerobically fermented in the peptone yeast extract glucose (PYG) medium at 37° C. for 2 to 3 days.

4.2 Preparation of Growth Factors

The skimmed milk and casein were mixed, centrifuged and ultra-filtered to obtain a crude extract of milk growth factor, including nutrients of vitamins, purines and/or pyrimidines.

4.3 Manufacture of Pharmaceutical Dosage Form 5 volumes (ml) of growth factor and 1 volume (ml) of protective agent (such as vitamin C, cysteine) were added to 100 volumes (ml) of the fermented bacterial solution of *Butyribacter intestini* TF01-11, fully stirred to be uniform, and then added with starch excipients (such as maltodextrin), thus obtaining the medicament or pharmaceutical dosage form containing *Butyribacter intestini* TF01-11.

Deposit of Microorganism

*Butyribacter intestini* TF01-11 is deposited in the China General Microbiological Culture Collection Center (CGMCC) on Jun. 16, 2015, with a deposit number of CGMCC 10984. The depository is located at the Institute of Microbiology, Chinese Academy of Sciences, No. 1, West Beichen Road, Chaoyang District, Beijing, China.

All publications mentioned herein are incorporated by reference as if each individual document was cited as a reference in the present application. It should also be understood that, after reading the above teachings of the present disclosure, those skilled in the art can make various changes or modifications, equivalents of which falls in the scope of claims as defined in the appended claims.

What is claimed is:

1. A method for treating inflammatory bowel disease in a subject in need thereof, comprising administering an effective amount of *Butyribacter intestini* TF01-11 under deposit number CGMCC 10984 or a composition comprising an effective amount of the *Butyribacter intestini* TF01-11 to the subject,
   wherein the inflammatory bowel disease comprises ulcerative colitis, general enteritis or a combination thereof.

2. A method capable of at least one of controlling weight loss, decreasing disease activity index (DAT) or relieving intestinal lesions in a subject having ulcerative colitis, the method comprising administering an effective amount of *Butyribacter intestini* TF01-11 under deposit number CGMCC 10984 or a composition comprising an effective amount of the *Butyribacter intestini* TF01-11 to the subject in need thereof.

3. The method according to claim 1, wherein the *Butyribacter intestini* TF01-11 or the composition is capable of one or more selected from the group consisting of:
   (i) controlling weight loss in a mammal;
   (ii) decreasing disease activity index (DAI) in a mammal; and
   (iii) relieving intestinal lesions in a mammal.

4. The method according to claim 1, wherein the composition is administrated orally.

5. The method according to claim 1, wherein the administration dosage is 0.01 to 5 g/50 kg body weight per day.

6. The method according to claim 1, wherein the composition is in a unit dosage form of one tablet, one capsule or one vial, and the composition in each unit dosage form is of a mass of 0.05 g to 5 g.

7. The method according to claim 1, wherein the subject includes human and non-human mammal.

8. The method according to claim 1, wherein the composition further comprises a food or pharmaceutically acceptable carrier.

9. The method according to claim 1, wherein the composition is selected from the group consisting of a food composition, a health care composition, a pharmaceutical composition, a beverage composition, a feed composition or a combination thereof.

10. The method according to claim 1, wherein the composition further comprises one or both of probiotics and prebiotics.

11. The method according to claim 10, wherein the probiotics are Lactic acid bacteria.

12. The method according to claim 10, wherein the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

13. The method according to claim 1, wherein the composition further comprises a substance capable of maintaining the viability of *Butyribacter intestini*.

14. The method according to claim 13, wherein the substance capable of maintaining the viability of *Butyribacter intestini* is selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof.

15. The method according to claim 1, wherein the composition comprises $1\times10$-$1\times10^{15}$ cfu/mL or cfu/g of *Butyribacter intestini* TF01-11 based on the total volume or total weight of the composition.

16. The method according to claim 1, wherein the composition contains 0.1 wt % to 90 wt % of *Butyribacter intestini* TF01-11 based on the total weight of the composition.

17. The method according to claim 10, wherein the probiotics comprise one or both of Bifidobacteria and *Lactobacillus acidophilus*.

18. The method according to claim 1, wherein the composition comprises $1\times10^4$-$1\times10^{10}$ cfu/mL or cfu/g of *Butyribacter intestini* TF01-11 based on the total volume or total weight of the composition.

* * * * *